US012605557B2

(12) United States Patent
Kuno et al.

(10) Patent No.: US 12,605,557 B2
(45) Date of Patent: Apr. 21, 2026

(54) AUTOMATED EXTERNAL DEFIBRILLATOR

(71) Applicant: Nihon Kohden Corporation, Tokyo (JP)

(72) Inventors: Ryosuke Kuno, Saitama (JP); Kanchi Ito, Saitama (JP); Yuji Igawa, Saitama (JP); Fumihito Iwai, Saitama (JP); Tsutomu Wakabayashi, Saitama (JP)

(73) Assignee: Nihon Kohden Corporation, Tokyo (JP)

( * ) Notice: Subject to any disclaimer, the term of this patent is extended or adjusted under 35 U.S.C. 154(b) by 458 days.

(21) Appl. No.: 18/000,624

(22) PCT Filed: Jun. 2, 2021

(86) PCT No.: PCT/JP2021/021056
§ 371 (c)(1),
(2) Date: Dec. 2, 2022

(87) PCT Pub. No.: WO2021/246452
PCT Pub. Date: Dec. 9, 2021

(65) Prior Publication Data
US 2023/0321452 A1     Oct. 12, 2023

(30) Foreign Application Priority Data

Jun. 5, 2020    (JP) ................................. 2020-098724

(51) Int. Cl.
*A61N 1/39*          (2006.01)
(52) U.S. Cl.
CPC ......... *A61N 1/3904* (2017.08); *A61N 1/3937* (2013.01); *A61N 1/3993* (2013.01)

(58) Field of Classification Search
CPC ............................ A61N 1/3904; A61N 1/3925
See application file for complete search history.

(56) References Cited

U.S. PATENT DOCUMENTS

| | | | | |
|---|---|---|---|---|
| 5,749,913 A | * | 5/1998 | Cole ...................... | A61B 5/333 607/59 |
| 5,797,969 A | * | 8/1998 | Olson .................. | A61N 1/3904 607/5 |

(Continued)

FOREIGN PATENT DOCUMENTS

| | | |
|---|---|---|
| CN | 104853804 A | 8/2015 |
| CN | 109843375 A | 6/2019 |

(Continued)

OTHER PUBLICATIONS

Office Action issued in Japanese Patent Application 2020-098724, mailed on Dec. 19, 2023, 7 pages including 4 pages of English translation.

(Continued)

*Primary Examiner* — Eric D. Bertram
(74) *Attorney, Agent, or Firm* — Dorsey & Whitney LLP

(57) ABSTRACT

An automated external defibrillator includes: an operation accepter that accepts an operation input from a user; and a self-test executor that executes a self-test for checking a state of the automated external defibrillator when a first condition or a second condition has been satisfied. The first condition is that a setting time instant set in advance comes. The second condition is that the operation accepter accepts a predetermined operation input.

7 Claims, 2 Drawing Sheets

(56) References Cited

U.S. PATENT DOCUMENTS

| | | | | |
|---|---|---|---|---|
| 5,897,576 A * | 4/1999 | Olson | | A61N 1/3904 |
| | | | | 607/7 |
| 5,955,956 A * | 9/1999 | Stendahl | | A61N 1/3904 |
| | | | | 340/657 |
| 5,999,493 A | 12/1999 | Olson | | |
| 6,088,616 A | 7/2000 | Olson et al. | | |
| 7,930,023 B2 * | 4/2011 | Vaisnys | | A61N 1/3904 |
| | | | | 607/5 |
| 10,029,108 B2 * | 7/2018 | Powers | | A61N 1/3904 |
| 2004/0133244 A1 | 7/2004 | Vaisnys et al. | | |
| 2006/0136000 A1 * | 6/2006 | Bowers | | A61N 1/3993 |
| | | | | 607/5 |
| 2006/0217775 A1 | 9/2006 | Mills et al. | | |
| 2008/0147136 A1 * | 6/2008 | Zhou | | A61N 1/3706 |
| | | | | 607/7 |
| 2010/0063556 A1 * | 3/2010 | Oestreich | | A61N 1/39044 |
| | | | | 600/16 |
| 2013/0317560 A1 * | 11/2013 | Barnes | | A61N 1/3925 |
| | | | | 607/6 |
| 2014/0031885 A1 | 1/2014 | Elghazzawi et al. | | |
| 2015/0265844 A1 * | 9/2015 | Powers | | A61N 1/3943 |
| | | | | 607/6 |
| 2016/0274162 A1 * | 9/2016 | Freeman | | A61N 1/39 |
| 2016/0294951 A1 | 10/2016 | Durrant et al. | | |
| 2017/0061168 A1 * | 3/2017 | Sundaram | | G06K 7/0095 |
| 2018/0296848 A1 | 10/2018 | Powers et al. | | |
| 2019/0099608 A1 | 4/2019 | Elghazzawi et al. | | |
| 2019/0232068 A1 | 8/2019 | Lancaster et al. | | |
| 2019/0232070 A1 * | 8/2019 | Lancaster | | A61N 1/3993 |
| 2019/0349435 A1 | 11/2019 | Durrant et al. | | |
| 2023/0241404 A1 * | 8/2023 | Kumamoto | | A61N 1/3993 |
| | | | | 607/5 |
| 2023/0254378 A1 | 8/2023 | Durrant et al. | | |

FOREIGN PATENT DOCUMENTS

| | | | |
|---|---|---|---|
| CN | 109952130 A | 6/2019 |
| JP | 2013240466 A | 12/2013 |
| JP | 2016500286 A | 1/2016 |
| JP | 2018515832 A | 6/2018 |
| JP | 2019530527 A | 10/2019 |
| WO | 2021246452 A1 | 12/2021 |

OTHER PUBLICATIONS

International Search Report and Written Opinion issued in International Application No. PCT/JP2021/021056, mailed on Sep. 23, 2021, 9 pages.

Office Action issued in Japanese Patent Application No. 2020-098724 issued on Apr. 23, 2024, 13 pages including 8 pages of English translation.

Office Action issued in Chinese Patent Application No. 202180040580.5, mailed on Dec. 25, 2025, 17 pages including 9 pages of English translation.

* cited by examiner

*FIG. 2*

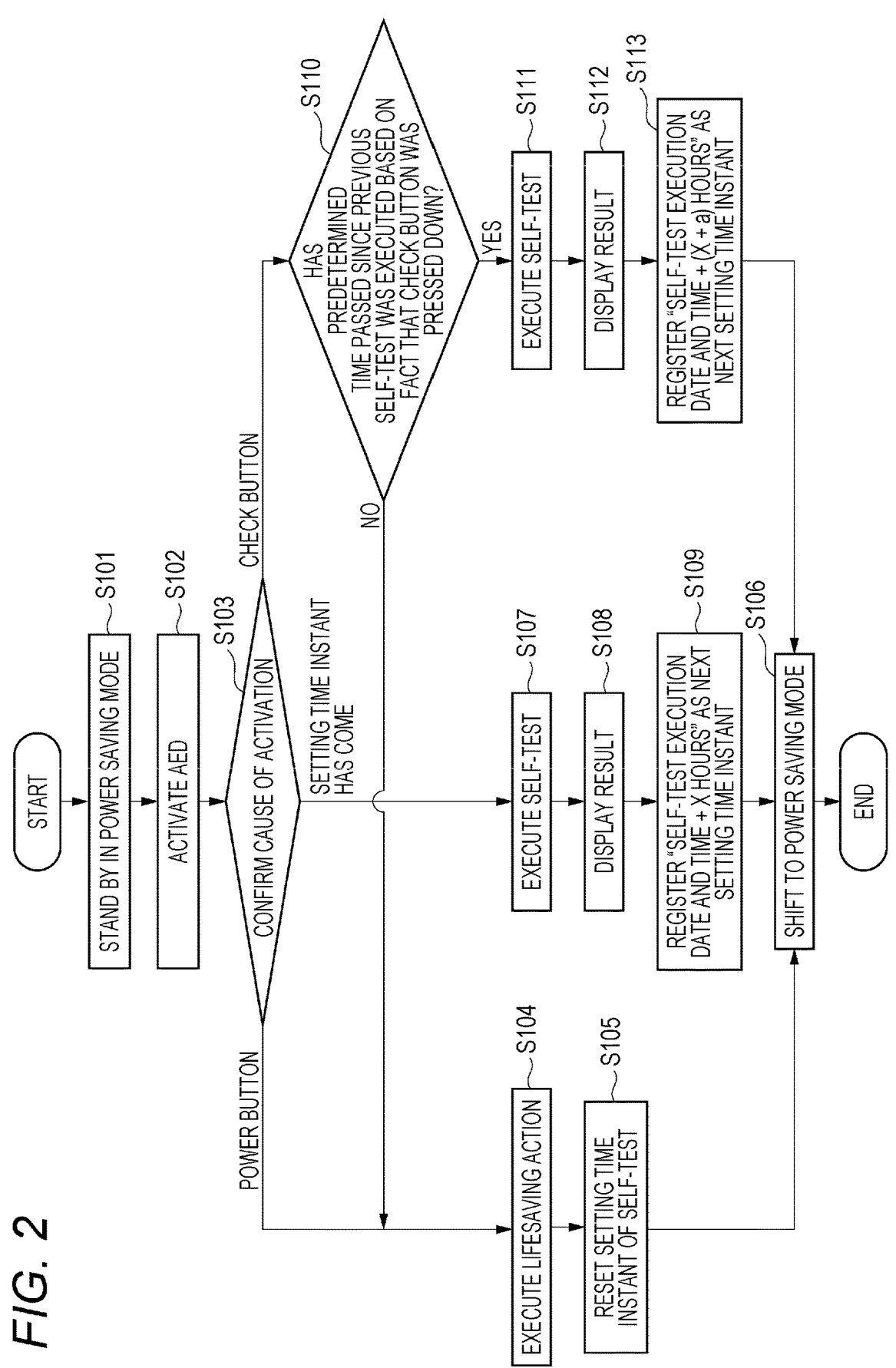

START

STAND BY IN POWER SAVING MODE — S101

ACTIVATE AED — S102

CONFIRM CAUSE OF ACTIVATION — S103

POWER BUTTON

EXECUTE LIFESAVING ACTION — S104

RESET SETTING TIME INSTANT OF SELF-TEST — S105

SETTING TIME INSTANT HAS COME

EXECUTE SELF-TEST — S107

DISPLAY RESULT — S108

REGISTER "SELF-TEST EXECUTION DATE AND TIME + X HOURS" AS NEXT SETTING TIME INSTANT — S109

SHIFT TO POWER SAVING MODE — S106

END

CHECK BUTTON

HAS PREDETERMINED TIME PASSED SINCE PREVIOUS SELF-TEST WAS EXECUTED BASED ON FACT THAT CHECK BUTTON WAS PRESSED DOWN? — S110

YES

EXECUTE SELF-TEST — S111

DISPLAY RESULT — S112

REGISTER "SELF-TEST EXECUTION DATE AND TIME + (X + a) HOURS" AS NEXT SETTING TIME INSTANT — S113

NO

AUTOMATED EXTERNAL DEFIBRILLATOR

This application is a 371 National Phase entry of PCT/JP2021/021056 filed on Jun. 2, 2021, which in turn claims priority to Japanese Patent Application No. 2020-98724 filed on Jun. 5, 2020, the entire contents of which are incorporated herein by reference.

TECHNICAL FIELD

The present disclosure relates to an automated external defibrillator.

BACKGROUND ART

Generally, automated external defibrillators (hereinafter also abbreviated to AEDs) are mounted with self-test functions. In such a self-test, for example, a remaining battery level, a connection state with a defibrillation pad, whether various circuits operate normally or not, etc. are checked so that it is determined whether the AED can be used normally or not.

The self-test is often automatically executed periodically, such as being performed at a predetermined time instant on a daily basis. For example, Patent Literature 1 discloses an AED provided with a function of automatically performing a self-test in a predetermined cycle and a function of postponing a timing of a next self-test when an override button has been pressed down.

CITATION LIST

Patent Literature

PTL 1: JP-T-2019-530527

SUMMARY OF INVENTION

Technical Problem

It is important that the self-test is automatically executed at a preset time instant so as to prevent occurrence of a situation that the self-test has not been performed for a long time. On the other hand, there may also arise a situation that a user wants to perform the self-test immediately. However, the background-art AED disclosed in Patent Literature 1 cannot perform the self-test at the timing desired by the user.

An object of the present disclosure is to provide an automated external defibrillator that can execute a self-test at any timing desired by a user while automatically performing the self-test at a preset time instant.

Solution to Problem

According to an aspect of the present disclosure, there is provided an automated external defibrillator including:

an operation accepter that accepts an operation input from a user; and a self-test executor that executes a self-test for checking a state of the automated external defibrillator when a first condition or a second condition has been satisfied; wherein:

the first condition is that a setting time instant set in advance comes; and the second condition is that the operation accepter accepts a predetermined operation input.

Advantageous Effects of Invention

According to the configuration of the aforementioned disclosure, it is possible to provide an automated external defibrillator that can execute a self-test even at any timing desired by a user while automatically performing the self-test at a time instant set in advance.

BRIEF DESCRIPTION OF DRAWINGS

FIG. 2 is a flowchart for explaining an example of an action process executed in the automated external defibrillator according to the embodiment of the present disclosure.

DESCRIPTION OF EMBODIMENT

Figure 1:
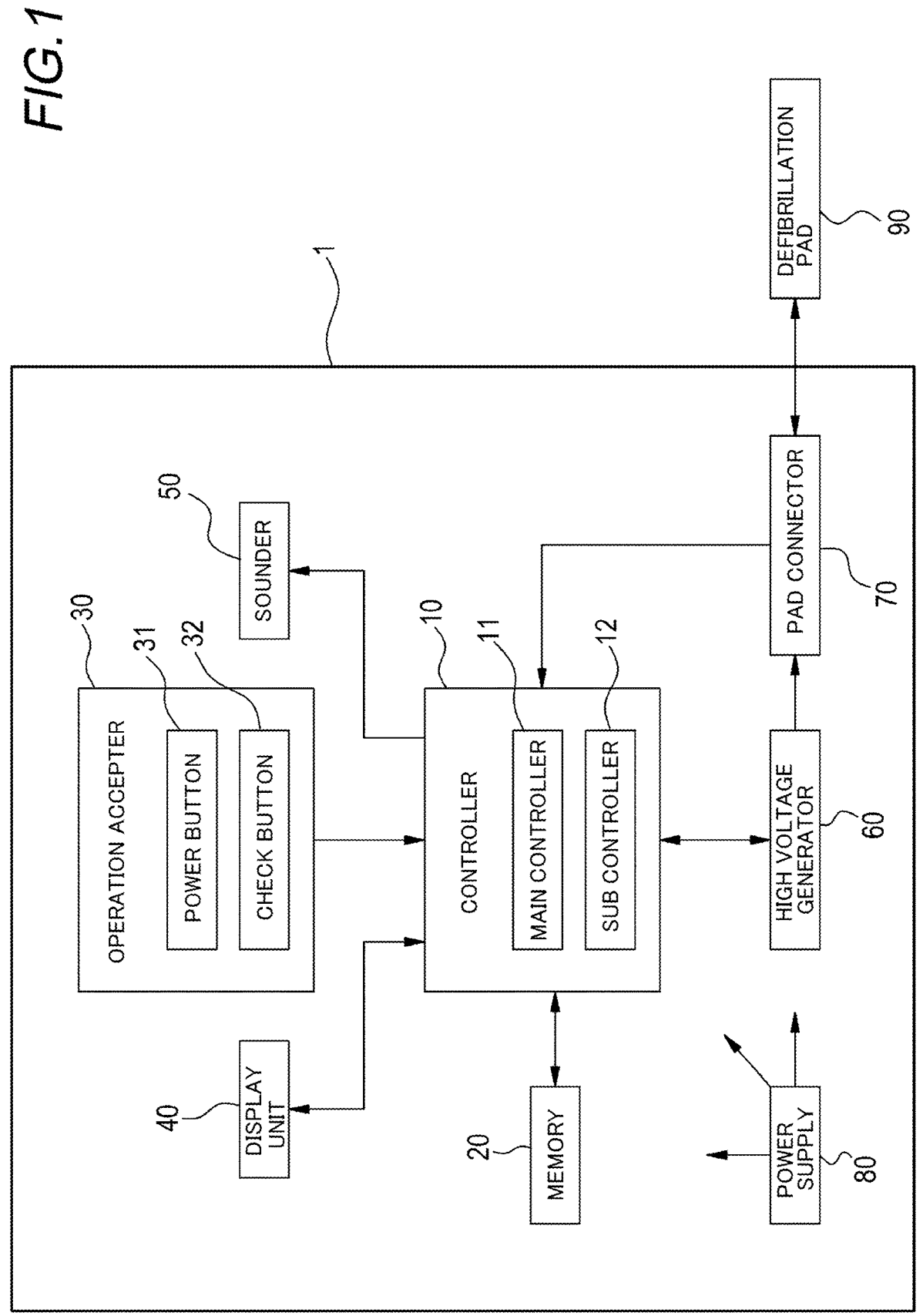
FIG. 1 is a block diagram for explaining an example of a configuration of an automated external defibrillator according to an embodiment of the present disclosure.

An embodiment of the present disclosure will be described below by way of example with reference to the drawings. Identical or equivalent elements will be designated by the same reference signs or names correspondingly and respective even in different drawings, and duplicate description thereof will be therefore omitted appropriately.
Configuration of Automated External Defibrillator (AED)

First, respective processors constituting an AED 1 will be described using FIG. 1. FIG. 1 is a block diagram showing an example of a configuration of the AED 1 according to the embodiment of the present disclosure. The AED 1 is provided with a controller 10, a memory 20, an operation accepter 30, a display unit 40, a sounder 50, a high voltage generator 60, a pad connector 70 and a power supply 80.

The controller 10 reads and executes a program etc. stored in the memory 20 to control various actions of the AED 1. The controller 10 includes a main controller 11 and a sub controller 12. Moreover, although not shown, the controller 10 has a real time clock and an A/D converter.

The main controller 11 includes a main CPU (Central Processing Unit) controlling the various actions in a state in which the AED 1 has been powered on. The main controller 11 controls the various actions for lifesaving (hereinafter also referred to as "lifesaving actions") such as energy charging/discharging control, sequence control, A/D conversion, and electrocardiogram analysis.

In addition, the main controller 11 controls execution of a self-test. That is, the main controller 11 has a function as a self-test executor. When a first condition or a second condition has been satisfied, the main controller 11 executes the self-test. A specific example of the first condition is that a setting time instant set in advance comes. A specific example of the second condition is that the operation accepter 30 accepts a predetermined operation input (such as pressing down a check button 32 that will be described later). In the self-test, for example, the main controller 11 performs check of a circuit for controlling lifesaving actions (such as confirmation of a time constant of an electrocardiogram input circuit, confirmation of a circuit recognizing paddle contact, and confirmation of an energy value during charging into a capacitor/during internal discharging), check of the power supply 80 (such as a voltage value, a remaining value of a battery, and a value of current consumption), check of a defibrillation pad 90 connected to the pad connector 70 (such as a resistance value of the pad and confirmation of expiry date for use), etc. to confirm whether they are normal or abnormal.

The main controller 11 sets a setting time instant for execution of a next self-test after completion of the lifesaving actions, after completion of the self-test, or the like. A method for determining the next setting time instant will be described in detail in the following paragraphs by use of FIG. 2. In addition, the main controller 11 may reset the next setting time instant at any time instant desired by a user based on an operation input of the user on the operation accepter 30. Incidentally, the "setting time instant" may designate date and time or may designate only time. Specifically, the "setting time instant" may be set as "YMDhm (Y=year, M=month, D=day, h=hour, and m=minute)" or may be set as "hm (h=hour and m=minute)".

The sub controller 12 includes a sub CPU controlling various actions such as supply of electric power to the main CPU of the main controller 11. When the power is off (e.g. when a power button 31 and the check button 32 which will be described later are not pressed down and the self-test is also not executed), electric power is not supplied to the main CPU of the main controller 11, and the AED 1 is in a standby state in a power saving mode. Incidentally, supply of electric power from the power supply 80 to the real time clock is performed even in the power saving mode. That is, the real time clock also performs time counting when the AED 1 is powered off.

When the power button 31 (a form of a first button) or the check button 32 (a form of a second button) which will be described later is pressed down or when the AED 1 is powered on due to a fact that the setting time instant set in advance has come, the sub controller 12 makes control to supply electric power from the power supply 80 to the main controller 11. In addition, the sub controller 12 transmits the cause of the power-on (the cause of activation of the AED 1) to the main controller 11.

The memory 20 stores a necessary program for action of the AED, audio data, an adjustment value, electrocardiogram data during lifesaving, a self-test history, etc. The memory may include, for example, a memory device such as an ROM (Read Only Memory) or an RAM (Random Access Memory), or a secondary memory device such as a hard disk. A part of the memory 20 may be an external memory device that can be detachably attached to the AED 1.

The operation accepter 30 accepts an operation input from the user. The operation accepter 30 includes the power button 31 and the check button 32. The power button 31 is a button for starting a lifesaving action. The check button 32 is a button for starting a self-test. In addition, although not shown, the operation accepter 30 may be provided with a shock button for executing an electric shock, a button for setting a setting time instant of the self-test, etc.

The display unit 40 displays, for example, a result of the self-test. The user can confirm the display unit 40 to confirm whether the AED 1 is normal or abnormal. The display unit 40 may be constituted by an LED (Light Emitting Diode) or may be constituted by a magnetic reversal disk or the like. In addition, the display unit 40 may be provided with a liquid crystal display for displaying an instruction to the user by a picture or characters or a display for displaying an electrocardiogram signal. In addition, the display unit 40 may be provided with a touch panel or may function also as the operation accepter 30.

The sounder 50 issues various instructions to the user by voice with reference to the audio data stored in the memory 20. In addition, when abnormality is found due to the self-test, the sounder 50 emits a warning sound to notify the user of the abnormality.

The high voltage generator 60 carries out charging and discharging of energy used for defibrillation in accordance with a control signal from the main controller 11. The pad connector 70 is connected to the defibrillation pad 90. The energy discharged by the high voltage generator 60 is transmitted to a person in need for lifesaving through the pad connector 70 and the defibrillation pad 90. In addition, the defibrillation pad 90 fetches an electrocardiogram signal of the person in need for lifesaving. The electrocardiogram signal is, for example, filtered and amplified before being transmitted to the main controller 11.

The power supply 80 includes the battery. The power supply 80 converts electric power supplied from the battery into a required voltage, and supplies the electric power to the aforementioned processors. The remaining level of the battery is confirmed by the self-test.

Action Example of AED

Next, an action example of the AED 1 will be described using FIG. 2. FIG. 2 is a flowchart showing an example of an action process executed in the AED 1 according to the embodiment of the present disclosure. Incidentally, various processings shown in FIG. 2 may be rearranged in sequence or executed in parallel as long as there is no contradiction.

First, the AED 1 which is in a powered off state stands by in a power saving mode (step S101). Next, when the AED 1 is powered on and electric power is supplied to the main CPU of the main controller 11, the AED 1 is activated (step S102). In addition, in the step S102, a cause of the activation of the AED 1 is transmitted from the sub controller 12 to the main controller 11.

Next, the main controller 11 confirms the cause of the activation of the AED 1 (step S103). Examples of the cause of the activation of the AED 1 include at least at least three kinds of facts, i.e. the fact that the power button 31 has been pressed down, the fact that a setting time instant for execution of a self-test has come, and the fact that the check button 32 has been pressed down.

When it is confirmed in the step S103 that the cause of the activation of the AED 1 is the fact that the power button 31 has been pressed down, the main controller 11 makes control to start a lifesaving action (step S104). When it is determined that an electric shock on a subject is required in the lifesaving action (when an electrocardiogram in which an electric shock is required is detected), the main controller 11 properly performs blinking a button for the electric shock, outputting electric energy in response to the fact that the button has been pressed down, etc.

Next, when the lifesaving action is completed, the main controller 11 resets the setting time instant of the self-test (step S105). For example, an original setting time instant which had been set before the AED 1 was activated in the step S102 may be reset as a setting time instant of a next self-test in the step S105. When the original setting time instant has come during the lifesaving action in the step S104, it is preferable that the self-test based on the fact that the setting time instant has come is not executed but the main controller 11, for example, sets, as the next setting time instant, a time instant after a second time from the original setting time instant. Here, the "second time" is not limited particularly. For example, the "second time" may be a time such as twelve hours, twenty-four hours or forty-eight hours. The "second time" is preferably twenty-four hours. In addition, the "second time" may have the same length as a "first time" that will be described later or may have a different length therefrom.

Next, the supply of the electric power to the main CPU of the main controller 11 is cut off, and the AED 1 shifts to the power saving mode (step S106). Then, a series of action processes related to the lifesaving action is ended.

On the other hand, when it is confirmed in the step S103 that the cause of the activation of the AED 1 is the fact that the setting time instant has come (the first condition has been satisfied), the main controller 11 makes control to execute the self-test (step S107). Incidentally, when the setting time instant has come during the lifesaving action in the step S104, as described above, processings of the steps S107 to S109 are not executed.

Next, the main controller 11 makes control to display a result of the self-test to the display unit 40 (step S108). Incidentally, when there is an abnormality in the result of the self-test, it is preferable that, for example, voice is also outputted from the sounder 50 to notify the user of the abnormality.

Next, the main controller 11 sets a next setting time instant of the self-test (step S109). In the step S109, it is preferable that the main controller 11, for example, sets a time instant after the first time (X hours) from the date and time at which the self-test was executed in the step S107 (that is, the original setting time instant which came in the step S102). Here, the "first time" is not limited particularly. For example, the "first time" may be a time such as twelve hours, twenty-four hours or forty-eight hours. It is preferable that the "first time" is twenty-four hours.

Next, the supply of the electric power to the main CPU of the main controller 11 is cut off, and the AED 1 shifts to the power saving mode (step S106). Then, the series of action processes related to the self-test based on the fact that the setting time instant has come is ended.

On the other hand, when it is confirmed in the step S103 that the cause of the activation of the AED 1 is the fact that the check button 32 has been pressed down (when the second condition has been satisfied), the process proceeds to processing of a step S110. In the step S110, it is determined whether or not a time instant at which the check button 32 has been pressed down this time is a time instant at which a predetermined time (such as fifteen seconds) has passed since a previous self-test was executed based on the fact that the check button 32 was pressed down.

When it is determined in the step S110 that the time instant at which the check button 32 has been pressed down this time is not the time instant at which the predetermined time has passed since the previous self-test was executed based on the fact that the check button 32 was pressed down (NO in the step S110), the self-test is not executed and the main controller 11 executes processing related to the life-saving action of the step S104.

On the other hand, when it is determined in the step S110 that the time instant at which the check button 32 has been pressed down this time is the time instant at which the predetermined time has passed since the previous self-test was executed based on the fact that the check button 32 was pressed down (YES in the step S110), the main controller 11 makes control to execute a self-test (step S111). Incidentally, when the setting time instant has come during the execution of the self-test in the step S111, the processings of the steps S107 to S109 are not executed.

Next, the main controller 11 makes control to display a result of the self-test on the display unit 40 (step S112). Processing of the step S112 is the same as the processing of the step S108.

Next, the main controller 11 sets a next setting time instant of the self-test (step S113). In the step S113, it is preferable that the main controller 11, for example, sets, as the next setting time instant, a time instant after a longer time (X+a hours) than the first time from the date and time at which the self-test was executed in the step S111 (i.e. the time instant at which the check button 32 was pressed down in the step S102). Here, it is preferable that the length "a" is a length shorter than the first time. For example, the length "a" may be a time such as ten minutes, thirty minutes or one hour.

Next, the supply of the electric power to the main CPU of the main controller 11 is cut off, and the AED 1 shifts to the power saving mode (step S106). Then, the series of action processes related to the self-test based on the fact that the check button 32 has been pressed down is ended.

Successively, an effect of the AED 1 according to the present embodiment will be described. Assume that the check button 32 for the self-test is not provided in the AED 1, but the AED 1 is, for example, configured in such a manner that start of a lifesaving action and start of the self-test can be separated by a difference in how to operate the power button 31 (e.g. a difference in how many times the power button 31 is pressed down or how long the power button 31 is pressed down). In this case, operation of the AED 1 becomes so complicated that there is a fear that the user gets confused under an emergent situation in which the lifesaving task is required. In addition, when the button for starting the lifesaving action is operated, the AED typically plays voice for instructing actions that should be taken by the user. When such a button is also used for inputting the self-test, the aforementioned voice is played during the self-test. Therefore, the user feels annoyed, and the electric power of the battery is also consumed. On the other hand, in the configuration in which the AED 1 is provided with the power button 31 and the check button 32 different from the power button 31, the aforementioned demerit can be cancelled so that the self-test at any timing can be started by a very simple operation.

In addition, the user may press down a wrong button by mistake under an emergent situation in which a lifesaving task is required. When the check button 32 has been pressed down again at a short interval after the check button 32 was pressed down, there is a high possibility that the second pressing-down has been made by mistake. When the self-test is executed again in such a case, there is a fear that the lifesaving task may be performed too late. When the check button has been pressed down again before a predetermined time has passed since the self-test was executed in response to the fact that the check button 32 was pressed down, the AED 1 does not execute a self-test but starts an action for lifesaving so as to prevent the lifesaving task from being performed too late.

In addition, the self-test executed again at a short interval from the previous self-test has a small effect but has a large demerit in electric power consumption of the battery. When the self-test has been executed in response to the fact that the check button 32 was pressed down, the AED 1 changes a setting time instant of a next self-test based on a time instant at which the self-test has been executed. Therefore, it is possible to prevent occurrence of a situation that the next self-test based on the fact that the setting time instant has come is executed immediately after the self-test based on the fact that the check button 32 was pressed down. Consequently, it is possible to suppress electric power consumption of the battery.

In addition, in the case where the self-test has been executed in response to the fact that the setting time instant came, the AED 1 sets, as the next setting time instant, a time instant after the first time from the time instant at which the self-test has been executed. With this configuration, the self-test is executed periodically whenever the first time passes.

On the other hand, in the case where the self-test has been executed in response to the fact that the check button 32 was pressed down, the AED 1 sets, as the next setting time instant, a time instant after a longer time than the first time from the time instant at which the self-test has been executed. Here, in the configuration where a self-test is executed automatically and periodically whenever the first time passes since a previous self-test was executed manually, assume that the user desires to execute the self-test manually whenever the first time passes. In this case, when a time instant at which the check button 32 is pressed down by the user is even a little late, the self-test is started in accordance with the fact that the setting time instant has come. In the case where the self-test has been executed in response to the fact that the check button 32 was pressed down, the AED 1 sets, as a next time instant, a time instant after a longer time than the first time from the time instant at which the self-test has been executed. With this setting, the situation that the self-test is executed automatically is prevented from occurring easily even if the user is only a little late for pressing down the check button 32. Such a configuration is particularly useful when the first time is twenty-four hours. Even if the user who desires to manually execute a self-test at a predetermined time instant on a daily basis performs the manual operation at a time instant slightly later than on the previous day, there is less possibility that the self-test might be started automatically.

Further, when the setting time instant has come during execution of a lifesaving action, the AED 1 does not execute a self-test based on the fact that the setting time instant has come. In this manner, the AED 1 prevents occurrence of a situation that the self-test is executed during the execution of the lifesaving action and the lifesaving action is hindered due to the self-test. In addition, in this case, the AED 1 automatically resets a next setting time instant. In this manner, the AED 1 prevents a situation that the self-test has not been executed for a long time.

The aforementioned embodiment is merely exemplar in order to make the presently disclosed subject matter easy to understand. The configuration according to the aforementioned embodiment can be changed/improved properly without departing from the gist of the presently disclosed subject matter.

REFERENCE SIGNS LIST

1: automated external defibrillator (AED)
10: controller
11: main controller (self-test executor)
12: sub controller
20: memory
30: operation accepter
31: power button
32: check button
40: display unit
50: sounder
60: high voltage generator
70: pad connector
80: power supply
90: defibrillation pad

The invention claimed is:

1. An automated external defibrillator comprising:
an operation accepter that accepts an operation input from a user; and
a self-test executor that executes a self-test for checking a state of the automated external defibrillator when a first condition or a second condition has been satisfied; wherein:
the first condition is that a setting time instant set in advance comes;
the second condition is that the operation accepter accepts a predetermined operation input;
the operation accepter has a first button that is a power button, and a second button for starting the self-test, the first button being different from the second button; and
the predetermined operation input is pressing down the second button, wherein
in response to the second button being pressed down again before a predetermined time has passed since the self-test was executed in response to a fact that the second button was pressed down, the automated external defibrillator starts an action for lifesaving.

2. The automated external defibrillator according to claim 1, wherein:
when the self-test has been executed in response to a fact that the second condition was satisfied, the self-test executor changes the setting time instant based on a time instant at which the self-test has been executed.

3. The automated external defibrillator according to claim 1, wherein:
when the self-test has been executed in response to a fact that the first condition was satisfied, the self-test executor sets, as a next setting time instant, a time instant after a first time from the time instant at which the self-test has been executed; and
when the self-test has been executed in response to a fact that the second condition was satisfied, the self-test executor sets, as a next setting time instant, a time instant after a longer time than the first time from the time instant at which the self-test has been executed.

4. The automated external defibrillator according to claim 1, wherein:
when the setting time instant has come during execution of an action for lifesaving, the self-test executor does not execute the self-test based on the fact that the setting time instant has come.

5. The automated external defibrillator according to claim 4, wherein:
when the setting time instant has come during the execution of the action for lifesaving, the self-test executor sets, as a next setting time instant, a time instant after a first time from the setting time instant.

6. The automated external defibrillator according to claim 1, further comprising:
a display unit that indicates that the self-test is in execution.

7. The automated external defibrillator according to claim 1, wherein in response to the first button being pressed down, the automated external defibrillator starts the action for lifesaving.

* * * * *